United States Patent [19]

Mehra

[11] Patent Number: 4,617,038

[45] Date of Patent: Oct. 14, 1986

[54] PROCESS FOR USING PREFERENTIAL PHYSICAL SOLVENTS FOR SELECTIVE PROCESSING OF HYDROCARBON GAS STREAMS

[75] Inventor: Yuv R. Mehra, Odessa, Tex.

[73] Assignee: El Paso Hydrocarbons Company, Odessa, Tex.

[21] Appl. No.: 784,566

[22] Filed: Oct. 4, 1985

Related U.S. Application Data

[63] Continuation-in-part of Ser. No. 759,327, Jul. 26, 1985, which is a continuation-in-part of Ser. No. 758,351, Jul. 24, 1985, which is a continuation-in-part of Ser. No. 637,210, Aug. 3, 1984, Pat. No. 4,578,094, which is a continuation-in-part of Ser. No. 532,005, Sep. 14, 1983, Pat. No. 4,526,594, which is a continuation-in-part of Ser. No. 507,564, Jun. 24, 1983, Pat. No. 4,511,381, which is a continuation-in-part of Ser. No. 374,270, May 3, 1982, Pat. No. 4,421,535.

[51] Int. Cl.$^4$ ............................................. F25J 3/00
[52] U.S. Cl. ........................................ 62/17; 62/20; 55/68
[58] Field of Search ............... 62/17, 18, 20; 55/68, 55/29, 30, 31; 203/66

[56] References Cited

U.S. PATENT DOCUMENTS

| | | | |
|---|---|---|---|
| 2,187,631 | 1/1940 | Schutt | 196/9 |
| 2,282,549 | 5/1942 | Sullivan, Jr. et al. | 196/9 |
| 2,325,379 | 7/1943 | Durrum | 202/40 |
| 2,357,028 | 8/1944 | Shiras et al. | 202/67 |
| 2,433,286 | 12/1947 | McKinnis | 202/39.5 |
| 2,455,803 | 12/1948 | Pierotti | 202/39.5 |
| 2,559,519 | 7/1951 | Smith, Jr. et al. | 202/39.5 |
| 2,570,066 | 10/1951 | Morrow et al. | 202/39.5 |
| 2,573,341 | 10/1951 | Kniel | 260/683 |
| 2,961,383 | 11/1960 | Black | 202/39.5 |
| 3,280,206 | 10/1966 | Scola et al. | 260/674 |
| 3,287,262 | 11/1966 | Jones | 208/341 |
| 3,292,380 | 12/1966 | Bucklin | 62/20 |
| 3,337,425 | 8/1967 | Binning et al. | 203/52 |
| 3,349,145 | 10/1967 | Uitti | 260/672 |
| 3,445,537 | 5/1969 | Luther et al. | 260/674 |
| 3,520,143 | 7/1970 | Becker | 62/28 |
| 3,607,734 | 9/1971 | Stafford, Sr. | 208/341 |
| 3,616,271 | 10/1971 | Copelin | 203/52 |
| 4,035,167 | 7/1977 | Starks | 55/57 |
| 4,150,962 | 4/1979 | Colton | 62/17 |
| 4,191,640 | 3/1980 | Chess et al. | 208/348 |
| 4,272,269 | 6/1981 | Hammond et al. | 62/17 |

OTHER PUBLICATIONS

"High CO$_2$-High H$_2$S Removal with Selexol Solvent", by John W. Sweny, 59th Annual GPA Convention, Mar. 17-19, 1980, Houston, Tex.

"Ethylene Purification by Absorption Process", by Kniel and Slager, Chemical Engineering Progress, vol. 43, No. 7, Jul. 1947, pp. 335-342.

"Humble's Avery Island Plant: High Safety at Low Cost", by J. J. Weatherby, Hydrocarbon Processing & Petroleum Refiner, Apr. 1962, vol. 41, No. 4, pp. 113-116.

"Gas Absorption", as Chapter 8 in Mass Transfer Operations, by Treybal, McGraw-Hill Book Company, Second Ed., 1968, pp. 221-226 and 393-395.

"Chemical Engineer's Handbook", Ed. by John H. Perry, McGraw-Hill Book Company, Fourth Ed., pp. 13-47 and 13-48.

Primary Examiner—Ronald C. Capossela
Attorney, Agent, or Firm—Depaoli & O'Brien

[57] ABSTRACT

A process is disclosed in which a preferential physical solvent selectively extracts and strips desirable C$_2$+ hydrocarbons from a raw hydrocarbon gas stream which is fed into the midsection of an Extractor-Stripper (ES) column, the rich solvent produced from the bottom thereof being regenerated in a distillation column which produces a hydrocarbon gas liquid stream as product and a lean physical solvent for recycling to the top of the ES column. When certain operating conditions and product specifications necessitate operating the ES column bottoms at a temperature high enough to become relatively energy inefficient, a single-stage intermediate flashing vessel is provided for effectively removing undesirable hydrocarbons at a pressure consistent with the operating pressure of the distillation column. The separated overhead vapor stream from the flashing vessel contains all of the undesirable components along with some desirable hydrocarbons. This stream is compressed to a pressure level consistent with the operating pressure of the ES column, and the compressed vapors are recycled to the ES column for additional recovery of desirable hydrocarbons.

16 Claims, 1 Drawing Figure

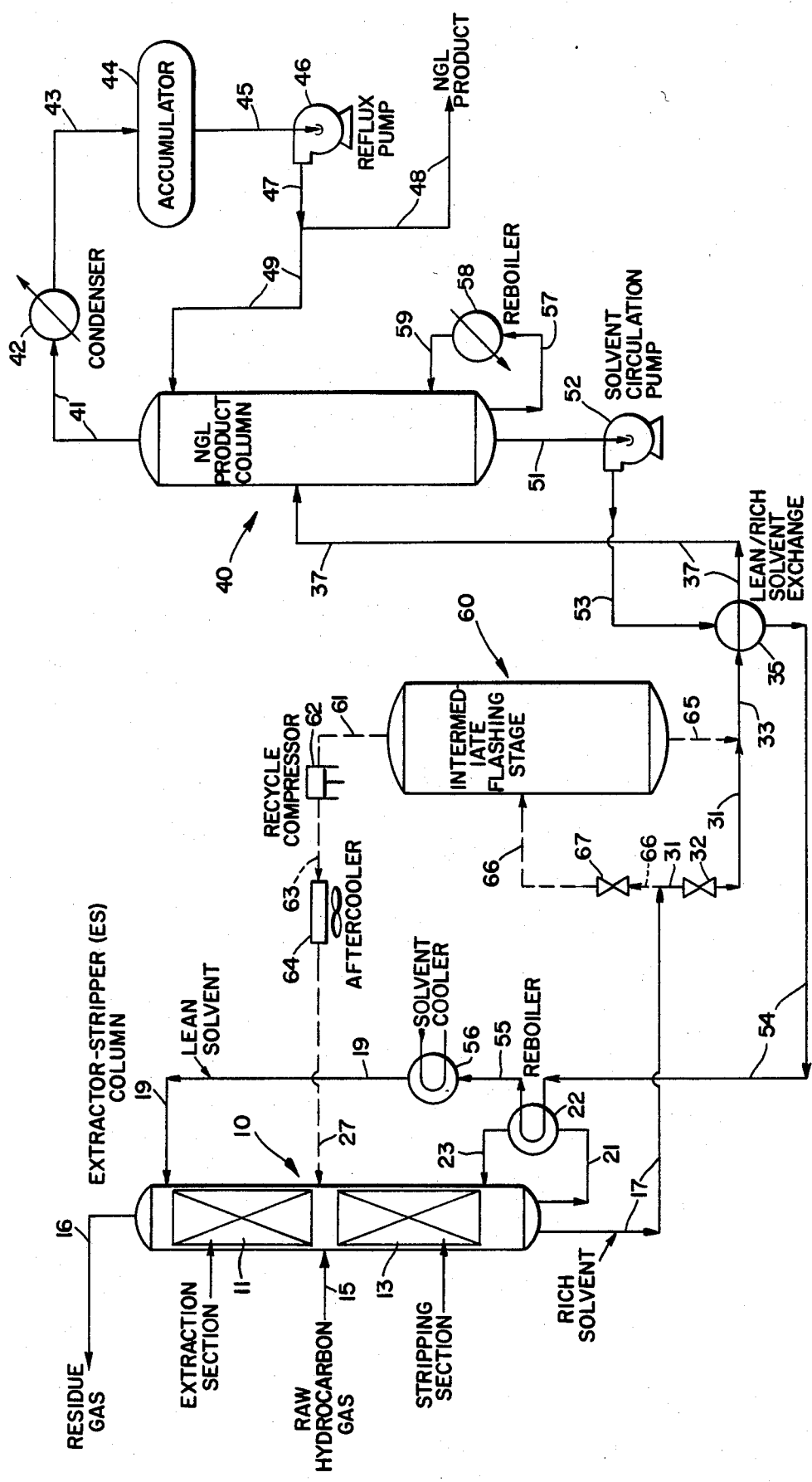

PROCESS FOR USING PREFERENTIAL PHYSICAL SOLVENTS FOR SELECTIVE PROCESSING OF HYDROCARBON GAS STREAMS

RELATED APPLICATIONS

This is a continuation-in-part of co-pending application Ser. No. 759,327, filed July 26, 1985, which is a continuation-in-part of co-pending application Ser. No. 758,351, filed July 24, 1985, which is a continuation-in-part of co-pending application Ser. No. 637,210, filed Aug. 3, 1984, now U.S. Pat. No. 4,578,094, which is a continuation-in-part of application Ser. No. 532,005, filed Sept. 14, 1983, now U.S. Pat. No. 4,526,594, which is a continuation-in-part of application Ser. No. 507,564, filed June 24, 1983, now U.S. Pat. No. 4,511,381, which is a continuation-in-part of application Ser. No. 374,270, filed May 3, 1982, now U.S. Pat. No. 4,421,535.

BACKGROUND OF THE INVENTION

1. Field of the Invention

This invention relates to contacting a hydrocarbon-containing gas stream with a physical solvent and particularly relates to contacting a hydrocarbon gas stream with a preferential physical solvent. It more specifically relates to separating and recovering ethane and higher boiling hydrocarbons from a hydrocarbon-containing gas stream and especially relates to simplification of the Mehra Process by elimination of the flashing step.

2. Review of the Prior Art

Hydrocarbons must often be recovered from such gas streams as hydrocarbon gas, alkylates, reformates, and the like. Many recovery processes are available, but countercurrently contacting the upwardly flowing gas stream with a downwardly flowing liquid under conditions furnishing high interfacial surface area is often a preferred recovery process, known as absorption or extraction.

Most physical solvents show some preference among hydrocarbons in a mixture thereof. In other words, they have greater solvency, perhaps because of a stronger physical attraction, for one or more hydrocarbons in such a mixture. This preference is measured by the absorption principle, leading to an alpha or relative volatility. Most of the commonly used lean oils, for example, have relative volatilities of methane over ethane of slightly less than 5.

Lean oils have been used in absorption plants for extracting $C_4+$ hydrocarbons, with some recovery of propane, from hydrocarbon gas streams for many years. The lean oils are non-selective for lighter hydrocarbons, such as ethane and propane, so that relatively large amounts of methane are abosrbed, thereby making the separation of ethane and propane from methane quite difficult and expensive. Due to the market demand for lighter hydrocarbons, such as ethane and propane, and the lack of selectivity of lean oils for such components, the absorption processes have been replaced by processes consisting of refrigerated oil absorption, simple refrigeration, cascaded refrigeration, Joule-Thompson, or cryogenic expander processes. The related Mehra Process patents and applications are directed toward physical solvents having strongly preferential characteristics. The Mehra Process thereby overcomes the disadvantages of non-selectivity of common lean oils for lighter hydrocarbons, such as ethane and propane.

Furthermore, the recovery levels of various hydrocarbons from the above processes used for the extraction of $C_2+$ hydrocarbons are quite inflexible. The Mehra Process overcomes the inflexibility drawback by effectively utilizing the selectivity characteristics of preferential physical solvents. Typical recoveries for these processes are compared in Table I.

TABLE I

| COMPARISON OF TYPICAL LIQUID RECOVERIES | | | | |
|---|---|---|---|---|
| EXTRACTION | ETHANE (%) | PRO-PANE (%) | BU-TANES (%) | GASO-LINE (%) |
| ABSORPTION | 4 | 24 | 75 | 87 |
| REFRIGERATED ABSORPTION | 15 | 65 | 90 | 95 |
| SIMPLE REFRIGERATION | 35 | 80 | 93 | 97 |
| CASCADED REFRIGERATION | 70 | 96 | 99 | 100 |
| JOULE-THOMPSON EXPANSION | 75 | 96 | 99 | 100 |
| TURBO-EXPANDER | 85 | 97 | 100 | 100 |
| MEHRA PROCESS | 2-98 | 2-99 | 2-100 | 100 |

In summary, the oil absorption, refrigerated oil absorption, simple refrigeration, and cascaded refrigeration processes operate at the pipeline pressures, without letting down the gas pressure, but the recovery of desirable liquids (ethane plus heavier components) is poor, with the exception of the cascaded refrigeration process which has extremely high operating costs but achieves good ethane and propane recoveries. The Joule-Thompson and cryogenic expander processes achieve high ethane recoveries by letting down the pressure of the entire inlet gas, which is primarily methane (typically 80–85%), but recompression of most of the inlet gas is quite expensive. The Mehra Process combines the advantages of the higher-pressure extraction processes by selectively recovering and letting down the pressure of essentially the desired components, thereby reducing the compression of undesirable components, such as methane, while achieving high levels of component recovery in a flexible manner.

In all of the above processes, except the Mehra Process, the ethane plus heavier components are recovered in a specific configuration determined by their composition in the raw hydrocarbon gas stream and equilibrium at the key operating conditions of pressure and temperature within the process.

Under poor economic conditions when the ethane price as petrochemical feedstock is less than its equivalent fuel price and when the propane price for feedstock usage is attractive, the operator of a hydrocarbon gas liquid extraction plant is limited as to operating choice because he is unable to minimize ethane recovery and maximize propane recovery in response to market conditions.

The refrigeration process, which typically recovers 80% of the propane, also typically requires the recovery of 35% of the ethane. In order to boost propane recovery to the 95+% level, cascaded refrigeration, Joule-Thompson, or cryogenic turbo-expander processes would have to be used while simultaneously boosting the ethane recovery to 70+% at a considerably larger capital investment.

The parent patents and applications related to the Mehra Process have utilized preferential physical solvents for recovering hydrocarbon gas liquids from hydrocarbon gas streams by extracting the hydrocarbon gas streams with a preferential physical solvent, flashing the rich solvent, and compressing, cooling, and condensing the desired $C_2+$ hydrocarbons. In carrying out the extraction of desired hydrocarbons, several streams had to be recycled, thereby requiring accessory equipment, such as compressors, coolers, condensers, associated piping, automatic control valves, pressure gauges, and data recording equipment. Furthermore, flashing of the rich solvent stream was carried out in multiple steps, consistent with economic criteria involving energy consumption and capital investment. Even though the energy consumption was lower for the Mehra Process than for conventional state-of-the-art processes, several steps were required that increased the complexity and overall capital requirements of such a plant. There is consequently a need for simplification of the Mehra Process in order to reduce its capital investment requirement.

U.S. Pat. No. 3,287,262 describes a process for contacting and recovering hydrocarbons such as hydrocarbon gasoline from raw or wet hydrocarbon gas. A lean oil which has been presaturated with ethane passes through an absorber countercurrently to a hydrocarbon gas stream to produce a rich oil which is sent to a de-ethanizer comprising a kettle section, a stripping section, and an absorbing section. From the bottom of this de-ethanizer, a kettle product or rich oil containing $C_3$-$C_6$ hydrocarbons is produced. From the top thereof an ethane stream is produced which is sent to a presaturator column in which lean oil passes downwardly to become presaturated with the ethane and form the ethane-presaturated feed for the absorber.

U.S. Pat. No. 3,520,143 shows in its FIG. 4 a washing or absorption process for purifying methane contaminated with ethane or ethylene. Propane, as the extraction liquid, is stripped in a stripping columr with heat to produce a stream of higher boiling hydrocarbons, such as ethane and ethylene, which is sent to a rectification column which also receives the liquefied gas mixture.

U.S. Pat. No. 3,607,734 is directed to the use of an integrated column for absorbing, demethanizing (or de-ethanizing or depropanizing), and splitting operations. Gaseous feed is then introduced to the absorber section, and liquid feed is then introduced to the absorber section and/or the splitter section. A light naphtha fraction from the splitter section is used as the primary absorbing medium in the absorber section. Heavy naphtha, also from the splitter section, is used as lean oil in a sponge section, at the very top of the column, primarily to remove light lean oil from the absorber section overhead. Absorber fat oil, light naphtha, heavy naphtha, bottoms, and fuel gas are or can be produced as products. This integrated column is intended to replace conventional process designs in which gas and liquid are fed to an absorber, overhead is fed to a sponge tower, and bottoms are fed to a splitter which produces overhead and bottoms. The splitter overhead is fed to a debutanizer which produces $C_4$ and lighter as overhead, light naphtha as an intermediate fraction, and intermediate naphtha as a bottom fraction. The bottoms from the splitter overhead are sent to a rerun tower which produces heavy naphtha as overhead and heating oil or catalyst feed as the bottoms fraction.

U.S. Pat. No. 4,191,640 is directed to a dual fractionating process for hydrocarbons which employs high pressure and low pressure fractionating zones. A stable hydrocarbon stream, such as propane, is introduced into one of the fractionating zones, this hydrocarbon stream being stable under the conditions existing in the high pressure fractionating zone and at least a portion of this hydrocarbon stream having a boiling point lower than the boiling point of at least one of the unstable components which accumulates in the high pressure fractionating zone. This process is directed to removing accumulations of unstable components in the lower section of the high pressure fractionating zone in the column. These unstable components are generally highly unsaturated in nature, e.g., acetylenes, dienes, and the like. If an ignition source is present, such as static electricity, detonation of these unstable components can occur.

In U.S. Pat. No. 4,150,962, high pressure hydrocarbon gas is sweetened with lean amines, dried with ethylene glycol, reduced in pressure in a turbo expander, scrubbed with a $C_4$ rich liquid, dried with a solid desiccant, and liquefied to form liquid methane. The rich stream from the scrubber is stripped in a fractionating column to remove methane, then stripped in another fractionating column to remove ethane, next stripped in a third fractionating column to remove propane, and then sent to a splitter to remove butane as overhead and $C_5+$ hydrocarbon as bottoms.

SUMMARY OF THE INVENTION

It is accordingly an object of this invention to provide a method for simplifying the arrangement of equipment needed for the Mehra Process.

It is another object to provide a continuous process for minimizing the capital investment needed for the Mehra Process.

It is a further object to utilize preferential physical solvents effectively for the selective extraction of $C_2+$ hydrocarbons from a hydrocarbon-containing gas stream.

It is an additional object to provide a process for selectively extracting desired hydrocarbon components from a hydrocarbon gas stream with a stream of a preferential physical solvent to produce a solvent rich in $C_1+$ hydrocarbons.

It is a still futher object to provide a process for selectively rejecting undesired hydrocarbons from the stream of $C_1+$-rich solvent.

In accordance with these objects and the principles of this invention, an improved Mehra Process is herein provided in which a raw gas stream is contacted with a preferential physical solvent in an Extractor-Stripper (ES) column. The gas enters the ES column below the extraction section and flows upwardly where it contacts lean preferential physical solvent which, after entering the extraction section at the top of the column, flows downwardly in a countercurrent manner. The contact takes place over mass transfer surfaces, such as packing or distillation trays. The solvent leaving at the bottom of the extraction section is rich in $C_1$ and heavier hydrocarbons.

This $C_1$-rich solvent enters the stripping section of the ES column and flows downwardly, where it comes in contact with the upward-flowing stripped hydrocarbons from the reboiler at the bottom of the ES column. The stripped hydrocarbons consist primarily of undesired hydrocarbons, such as $C_1$ if the desired objective is recovery of Chd $2+$ hydrocarbons, or $C_1$ and $C_2$ if the desired objective is the recovery of $C_3+$ hydrocarbons, and so forth, depending upon the desired recovery objectives.

The selective recovery of $C_2+$ components is controlled by variations in flow rates of lean preferential physical solvent by the extraction section of the ES column. Additional selectivity in this invention is provided by adding a reboiler and a stripping section in the extraction column, thereby gaining one more degree of freedom. This additional degree of freedom is effectively utilized by appropriately selecting the reboiling temperature in order to produce the rich solvent stream, consisting essentially of only the economically desired hydrocarbons, and rejecting the economically undesired hydrocarbons. Instead of a reboiler, a stripping stream of inert gas may be utilized for selective rejection of the undesirable hydrocarbons.

The rejected undesirable hydrocarbon stream, flowing upwardly through the stripping section of the ES column, does contain some of the desirable hydrocarbons which are recovered preferentially by the mass transfer principles developed for distillation as it flows over the packing or trays of the ES column. The hydrocarbons, stripped from the rich solvent, leave the stripping section of the ES column, join the incoming raw gas stream and flow together upwardly in the extraction section of the ES column, where lean physical solvent preferentially recovers any contained desired hydrocarbons.

The rich solvent leaving from the bottom of the ES column is let down in pressure to a pressure level consistent with the operation of the NGL (natural gas liquids) product column. This pressure level also obviates the need for a downstream compressor or pump. The rich solvent may be economically heated before entering the final NGL product column in order to lower the reboiler heat load and improve separation of hydrocarbons from the physical solvent.

The final NGL product column is a typical fractionation-type column in which the selectively extracted hydrocarbons are separated from the preferential physical solvent. The desired hydrocarbons are recovered from the top of the NGL product column while the hot, lean solvent leaves from the bottom of the NGL product column. The temperature at the bottom of the NGL product column is selected to ensure the recovery of all desirable hydrocarbons and is no higher than the boiling point of the physical solvent at the operating pressure. In order to minimize the loss of the physical solvent with the hydrocarbon gas liquid (NGL) product, the column overhead is refluxed with the condensed hydrocarbons.

In order to minimize the energy consumption within this process of this invention, the hot, lean physical solvent, leaving from the bottom of the NGL product column, is effectively utilized for heating the rich solvent feed to the NGL product column and for reboiling the ES column before returning to the top of the extraction section of the ES column as cool, lean preferential physical solvent.

It is important to note that in the process described so far, there is no external recycle of any streams. Furthermore, this process has been essentially reduced to a two-step process. Thus, the capital requirements of this process are considerably reduced over the previous versions of the Mehra process, as described in U.S. Pat. Nos. 4,421,535, 4,511,381, 4,525,594, and 4,578,094 and in applications Ser. Nos. 758,351, and 759,327, all of which are incorporated herein by reference.

This two-step version of the Mehra Process necessitates that the rich solvent, leaving the bottom of the ES column, contain only the specified amounts of the undesirable lighter components, such as $C_1$ in $C_2+$ products, in order to meet the NGL product specifications (if the hydrocarbon gas is natural gas). In previous versions of the Mehra process, this specification has been effectively achieved by selecting the operating pressure and temperature at the bottom of the demethanizing or stripping step. Because such a purity requirement has been combined with selectivity in the ES column of this invention, wherein the selection capability of operating pressure is unavailable because it is generally determined by the delivery pressure of the residue gas, only temperature flexibility at the bottom of the ES column is available for meeting the required specification of undesirable components because the other flexibility of flow rate of preferential physical solvent to the ES column is effectively utilized in meeting the selective recovery levels of desired hydrocarbon components of the raw gas stream.

In summary, the extraction section of the ES column is used for extracting desired hydrocarbon components from the hydrocarbon gas stream to form an extracted liquid at the bottom of the ES column, and the stripping section of the ES column is used for rejecting the undesired components from the extracted liquid. Under certain operating conditions and for certain NGL product specifications, it may become necessary to operate the ES column bottoms at temperatures high enough to become relatively energy inefficient. It may thus be economically viable and preferred to allow additional quantities of undesirable hydrocarbons to be present in the rich solvent leaving from the bottom of the ES column. These contained undesirable hydrocarbons would lower the temperature at the bottom of the ES column and thus allow for an effective energy recovery loop composed of rich/lean solvent streams.

The contained undesirable hydrocarbons can be effectively removed by providing a single-stage intermediate flashing vessel, operating at a pressure consistent with the operating pressure of the NGL product column. The separated vapor stream contains all of the undesirable components along with some desirable hydrocarbons. This stream is compressed to the pressure levels consistent with the operating pressure of the ES column. The compressed vapors are recycled to the ES column for additional recovery of desirable hydrocarbons.

The operating pressure and the temperature conditions of the ES column can vary from 300 to 1300 psig and 0° to 600° F., respectively, 400 to 600 psig being preferred operating pressure range for the ES column. Similarly, the operating pressure and temperature at the bottom of the NGL product column can vary from 10 to 500 psig and 150° to 800° F., respectively, 150 to 350 psig being a preferred range of operation for the NGL product column. The operating temperature at the top of the NGL product column is determined by the equilibrium conditions for the desired composition of the hydrocarbon liquid product that are consistent with the market conditions and the operating pressure of the column. The operating pressure of the NGL product column is selected such that the desired hydrocarbon can be condensed by reasonably available cooling media such as ambient air, cooling water, or warm level refrigerant. The bottoms temperature of the NGL product column is preferred to be equivalent to the boiling point of the physical solvent at the operating pressure in order to ensure maximum recovery of desirable hydrocarbons.

The preferential physical solvents are defined for the purposes of this invention as having a minimum relative volatility of methane over ethane of at least 5.0 (thereby defining its improved selectivity toward ethane over methane) and in addition a solubility of at least 0.25 standard cubic feet of gaseous hydrocarbons per gallon of the solvent (SCF/GAL) (thereby defining its hydrocarbon loading capacity), or, alternatively, a preferential factor of at least 1.25. The preferential factor for physical solvent selection for the Mehra Process is defined as a product of relative volatility of methane over ethane multiplied by the solubility of ethane in physical solvents, specified as standard cubic feet of ethane per gallon (SCF/gal). However, the ideal preferential physical solvent would have a selectivity toward ethane over methane of at least 10.0 and would simultaneously possess a hydrocarbon loading capacity of at least 3.0 SCF/GAL. This combination of minimum relative volatility and minimum solubility enables solvent flow rate variations and operating pressure variations to be selectively utilized in the Mehra Process for flexibly producing liquid products having selected hydrocarbon compositions.

For example, the relative volatility for methane with respect to ethane in the presence of dimethyl ether or polyethylene glycol (DMPEG) is 6.4, indicating that it is more selective toward ethane than many other absorption liquids. As other examples, N-methyl pyrrolidone (NMP) and dimethyl formamide (DMF) have relative volatilities of methane/ethane of 5.3 and 8.5, respectively. However, the solubility of hydrocarbons in NMP is 0.03 standard cubic feet per gallon (SCF/GAL) and in DMF is 0.04 SCF/GAL; these values are low when compared to 1.0 SCF/GAL for DMPEG. It is the combination of these factors that determines the effectiveness of physical solvents. In general, if a choice must be made, it is better to have a high preference factor than a high loading factor, although high levels of both factors are needed for really good performance in the Mehra Process.

Combined preferential factors are given in the following table for a common lean oil, NMP, DMF, proprietary solvent A, the minimum solvent having desired requirements for Mehra Process applications, DMPEG, and the minimum preferred level for the ideal solvent in the Mehra Process. These preferential factors are important because they inversely indicate the amount of solvent which is required, in terms of solvent flow rate, for a given recovery level of desirable hydrocarbons. In other words, as 6.4 is much greater than 0.16, the amount of NMP required is 40 times the amount of DMPEG required for the same performance.

heavier hydrocarbons. Using the same solvent, the process of this invention can achieve any desired propane recovery from 2% to 99+%, while recovering 99+% of butanes and all heavier hydrocarbons without recovering more than 2% of ethane.

This invention process produces a liquid hydrocarbon product having a composition which is selectively versatile rather than fixed, as in prior art processes. In consequence, the composition of this hydrocarbon product, as in the previously disclosed embodiments of the Mehra Process, can be readily adjusted in accordance with market conditions so that profitability of the absorption operation can be maximized at all times and on short notice. Such versatility is achieved by flexibility in operating additions and steps. Specifically, the operator must consider and selectively change or vary the flow rate of the preferential solvent with respect to the flow rate of the hydrocarbon gas stream. The flow rate may be varied within the range of 0.001–0.5 gallon of solvent per standard cubic foot of hydrocarbon gas, such as natural gas. He must additionally selectively vary the temperature at the bottom of the ES column.

Selectively rejecting methane, methane plus ethane, methane plus ethane plus propane, or methane plus ethane plus propane plus butanes takes place within the ES column. Depending upon the liquid product specifications and the inlet hydrocarbon gas composition, the rejecting of undesirable hydrocarbons occurs in accordance with the temperature at the bottom of the ES column. Essentially, the stripping section of the ES column functions much like the demethanizing or stripping step of the basic Mehra process because in the stripping section, emphasis is placed on keeping undesired lighter hydrocarbons from coming down the column. In the extraction section, in contrast, emphasis is placed upon keeping the desired heavier components from continuing up the column and exiting as a part of the residue gas.

Thus, in a process for the removal of hydrocarbon gas liquids, comprising hydrocarbons heavier than methane from a hydrocarbon gas stream, wherein a need exists for recovering to any selected degree and at extremely high recoveries a selected hydrocarbon component and all heavier hydrocarbonw within the group consisting of ethane, propane, butane, pentane, and heavier hydrocarbons, without the need simultaneously to recover hydrocarbons lighter than the selected hydrocarbon component from the hydrocarbon gas stream, this invention provides the improvement of selectively extracting the hydrocarbon gas liquid from the hydrocarbon gas stream with a preferential physical

TABLE II

| | Preferential Factors Defining Physical Solvents for Mehra Process Applications | | | | | | |
|---|---|---|---|---|---|---|---|
| SOLVENT | NMP | DMF | LEAN OIL | MIN. | DMPEG | Prop. A | MIN. FOR IDEAL |
| Alpha, α | 5.3 | 8.5 | 4.8 | 5.0 | 6.4 | 6.9 | 10.0 |
| Solubility, SCF/gal., γ | 0.03 | 0.04 | 0.2 | 0.25 | 1.0 | 4.2 | 3.0 |
| Preferential factor (α × γ) | 0.16 | 0.34 | 0.96 | 1.25 | 6.4 | 29.0 | 30.0 |

The process of this invention uses a preferential physical solvent for extracting ethane and heavier hydrocarbon components from a gas stream, such as a hydrocarbon gas stream, at any desired ethane recovery from 2% to 98% while recovering 99+% of propane and all solvent which provides selective capability for recovery according to the selected degree of (a) ethane in amounts ranging from 2–98%, (b) propane in amounts ranging from 2–99%, (c) butane in amounts ranging from 2–100%, or (d) pentane and higher molecular weight hydrocarbons in amounts ranging up to 100% which comprises:

A. selectively extracting and stripping the hydrocarbon gas stream with the physical solvent to produce a residue hydrocarbon gas stream of pipeline specifications and a rich solvent stream containing ethane and heavier hydrocarbons components, the solvent being selective for ethane and heavier hydrocarbon components of the gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor, determined by the multiplication of relative volatility of methane over ethane by the solubility of ethane in solvent, in SCF of ethane per gallon of solvent, is at least 1.25; and B. distilling the rich solvent to produce the hydrocarbon gas liquids and the physical solvent.

The invention may be further defined as an improvement in a process for selectively extracting hydrocarbon gas liquids from a hydrocarbon gas stream with a preferential physical solvent which provides selective capability for recovery according to the selected degree of (a) ethane in amounts ranging from 2–98%, (b) propane in amounts ranging from 2–99%, (c) butanes in amounts ranging from 2–100%, or (d) pentanes and higher molecular weight hydrocarbons in amounts ranging up to 100%, wherein a need exists for improving profitability by simplifying process design and by minimizing capital and maintenance costs. This improvement comprises:

A. selectively extracting and stripping the hydrocarbon gas stream with the physical solvent to produce a residue hydrocarbon gas stream of pipeline specifications and a rich solvent stream containing ethane and heavier hydrocarbon components, the solvent being selective for ethane and heavier hydrocarbon components of the gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor, determined by the multiplication of relative volatility of methane over ethane by the solubility of ethane in solvent, in SCF of ethane per gallon of solvent, is at least 1.25; and B. distilling the rich solvent to produce the hydrocarbon gas liquids and the physical solvent.

If the hydrocarbon gas stream is sour, it is preferred that it be sweetened by contact with an acid-absorbing solvent, such as an amine, for example, before the extraction-stripping process of this invention is utilized. However, if an amine pretreating step is not suitable, the sour hydrocarbon gas stream can be treated according to the instant process. The acidic components are then maintanied in liquid-phase or vapor-phase solution or contact, respectively, with the heavier hydrocarbon components until the solution or mixture, as a liquid, can be contacted by an acid-absorbing solvent. Because such post-absorption sweetening is done in liquid phase, the capital cost for equipment is relatively low.

BRIEF DESCRIPTION OF THE DRAWING

The FIGURE shows a schematic flow sheet for a process, having an Extractor-Stripper column and a distillation column, in which a preferential physical solvent extracts and strips selected $C_2+$ hydrocarbons from a hydrocarbon-containing raw hydrocarbon gas that is fed into the midsection of the extractor-stripper column and in which the rich solvent is regenerated in the distillation column which also produces a hydrocarbon liquid product as overhead.

DESCRIPTION OF THE PREFERRED EMBODIMENTS

As shown in the drawing, the improved Mehra Process of this invention for selective extraction of hydrocarbon liquids from a gas stream, which can be the extraction of natural gas liquids from a stream of raw natural gas, comprises combined extraction and stripping to form a rich solvent and a residue gas followed by distillation of the rich solvent to form the hydrocarbon gas liquid product and recycling of the lean solvent to the Extractor-Stripper column.

The Extractor-Stripper (ES) column 10 comprises an extraction section 11 in its upper portion and a stripping section 13 in its lower portion. These sections 11, 13 may be mounted in separate columns. Raw hydrocarbon gas, such as a natural gas, in line 15 enters the midsection, between sections 11 and 13, of column 10 and passes countercurrently to a preferential physical solvent entering the top of extraction section 11 through line 19. Stripped vapors from stripping section 13 also rise with the entering hydrocarbon gas and meet the downwardly moving solvent. The solvent is lean with respect to hydrocarbons, "lean" being defined as any hydrocarbon content below saturation. In an alternative embodiment, the raw hydrocarbon gas in line 15 is also combined with recycled gas entering the midsection of ES column 10 through line 27.

The solvent leaving extraction section 11, carrying absorbed $C_1+$ hydrocarbons, enters the top of stripping section 13 and passes countercurrently to vapors stripped from a pool of liquid in the bottom of column 10. This pool of liquid is kept at a selected boiling temperature and is boiled at a selected rate by heat which is produced in reboiler 22 as recirculated solvent in line 21 passes therethrough, receives heat from the lean solvent in line 54, and returns through line 23 to the bottom of column 10. This lean solvent gives up additional heat in solvent cooler 56 before entering the top of ES column 10 through line 19.

The rich solvent in line 17 from the bottom of column 10 passes from line 17 and line 31 to valve 32 and then, at the point of juncture with alternative line 65, into line 33 before entering heat exchanger 35 for lean/rich solvent exchange. The warmed solvent in line 37 is next fed to the midsection of NGL product column 40. The overhead leaves in line 41, passes through condenser 42, and discharges through line 43 into accumulator 44 from which liquid passes through line 45 to reflux pump 46. Pumped liquid in line 47 is partially returned to column 40 through line 49 as reflux, and the remaining amount is discharged as $C_2+$ hydrocarbon liquid product (NGL product in the drawing) through line 48.

Bottoms from column 40 are discharged through line 51 to pump 52 as lean solvent for passage through line 53, exchanger 35, line 54, reboiler 22, line 55, and solvent cooler 56 before entering the top of ES column 10 through line 19. The liquid in the bottom of NGL product column 40 is maintained at a selected temperature by recirculation through line 57, reboiler 58, and line 59.

As an alternative embodiment, rich solvent in line 17 is sent through line 66 and valve 67 to intermediate flashing stage 60 which produces an overhead of flashed gases in line 61 which are compressed by recycle compressor 62 and passed through line 63 and aftercooler 64 before entering line 27 and feeding to the midsection of ES column 10. Bottoms from intermediate flashing stage 60 are discharged through line 65 to enter line 33, pass through exchanger 35, and enter the midsection of NGL product column 40 through line 37.

Because it will be readily apparent to those skilled in the art of treating hydrocarbon gases that innumerable variations, modifications, applications, and extensions of the examples and principles hereinbefore set forth can be made without departing from the spirit and the scope of the invention, what is hereby defined as such scope and is desired to be protected should be measured, and the invention should be limited, only by the following claims.

What is claimed is:

1. In a process for the removal of hydrocarbon gas liquids, comprising hydrocarbons heavier than methane, from a hydrocarbon gas stream, wherein a need exists for recovering to any selected degree and at extremely high recoveries a selected hydrocarbon component and heavier hydrocarbons within the group consisting of ethane, propane, butane, and pentane without the need simultaneously to recover hydrocarbons lighter than said selected hydrocarbon component from said hydrocarbon gas stream, the improvement of selectively extracting said hydrocarbon gas liquids from said hydrocarbon gas stream with a preferential physical solvent which provides selective capability for recovery according to said selected degree of (a) ethane in amounts ranging from 2–98%, (b) propane in amounts ranging from 2–99%, (c) butane in amounts ranging from 2–100%, or (d) pentanes and higher molecular weight hydrocarbons in amounts ranging up to 100% which comprises:

A. selectively extracting and stripping said hydrocarbon gas stream with said physical solvent to produce a residue hydrocarbon gas stream of pipeline specifications and a rich solvent stream containing ethane and heavier hydrocarbon components, said physical solvent being selective for ethane and heavier hydrocarbon components of the gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor determined by the multiplication of relative volatility of methane over ethane by the solubility of ethane in solvent, in standard cubic feet of ethane per gallon of solvent, of at least 1.25; and B. distilling said rich solvent to produce said hydrocarbon gas liquids and said physical solvent.

2. In a process for selectively extracting hydrocarbon gas liquids from a hydrocarbon gas stream with a preferential physical solvent which provides selective capability for recovery according to said selected degree of (a) ethane in amounts ranging from 2–98%, (b) propane in amounts ranging from 2–99%, (c) butane in amounts ranging from 2–100%, or (d) pentanes and higher molecular weight hydrocarbons in amounts ranging up to 100%, wherein a need exists for improving profitability by simplifying process design and minimizing capital and maintenance costs, the improvement which comprises:

A. selectively extracting and stripping said hydrocarbon gas stream with said physical solvent to produce a residue hydrocarbon gas stream of pipeline specifications and a rich solvent stream containing ethane and heavier hydrocarbon components, said physical solvent being selective for ethane and heavier hydrocarbon components of the gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor, determined by the multiplication of relative volatility of methane over ethane by the solubility of ethane in solvent, in standard cubic feet of ethane per gallon of solvent, is at least 1.25; and B. distilling said rich solvent to produce said hydrocarbon gas liquids and said physical solvent.

3. In a process for the removal of hydrocarbon gas liquids comprising hydrocarbons heavier than methane from a hydrocarbon gas stream, wherein a need exists for recovering to any selected degree and at extremely high recoveries a selected hydrocarbon component and heavier hydrocarbons within the group consisting of ethane, propane, butane, and pentane without the need simultaneously to recover hydrocarbons lighter than said selected hydrocarbon component from said hydrocarbon gas stream, the improvement comprising: providing the capability of selectively extracting said hydrocarbon gas liquids from said hydrocarbon gas stream with a preferential physical solvent according to said selected degree of (a) ethane in amounts ranging from 2–98% (b) propane in amounts ranging from 2–99%, (c) butane in amounts ranging from 2–100%, or (d) pentanes and higher molecular weight hydrocarbons in amounts ranging up to 100% by:

A. contacting said hydrocarbon gas stream with said physical solvent at flow rates within the range of 0.001–0.5 gallon of solvent per standard cubic foot of hydrocarbon gas to produce a residue hydrocarbon gas stream of pipeline specifications and a downwardly moving solvent stream enriched in economically desirable hydrocarbon components, said solvent being selective for ethane and heavier hydrocarbon components of said gas stream such that: (1) the relative volatility of methane over ethane is at least 5.0 and the hydrocarbon loading capacity, defined as solubility of ethane in solvent, is at least 0.25 standard cubic feet of ethane per gallon of solvent, or (2) the preferential factor determined by the multiplication of relative volatility of methane over ethane by the solubility of ethane in solvent, in standard cubic feet of ethane per gallon of solvent, is at least 1.25;

B. stripping said downwardly moving solvent stream with an upwardly moving stream of stripped hydrocarbons to produce a stream of undesirable hydrocarbons, for mixing with said hydrocarbon gas stream, and a rich solvent stream containing said desirable hydrocarbon components; and C. distilling said rich solvent stream to produce said hydrocarbon gas liquids and said physical solvent.

4. The process of claims 1, 2 or 3, wherein said contacting of said step A is at pipeline pressures and wherein said flow rate of said physical solvent is selectively adjusted in response to market conditions.

5. The process of claim 4, wherein additional selectivity is provided by using a reboiler and a stripping section in an extraction column for carrying out said selectively extracting and stripping of said hydrocarbon gas stream with said preferential physical solvent, thereby gaining an additional degree of freedom.

6. The process of claim 5, wherein said additional degree of freedom is effectively utilized by appropriately selecting the reboiling temperature at the bottom of said column in order to produce said rich solvent stream consisting essentially of only said economically desirable hydrocarbons.

7. The process of claim 6, wherein said rejected undesirable hydrocarbon stream, flowing upwardly through said stripping section of said column, contains some desirable hydrocarbons which are recovered preferentially by mass transfer principles by transfer to said physical solvent.

8. The process of claim 7, wherein said hydrocarbons, stripped from said rich solvent, leave said stripping section of said column and join the incoming hydrocarbon gas stream and flow together upwardly in said extraction section of said column, wherein said lean solvent preferentially recovers any contained desired hydrocarbons.

9. The process of claim 8, wherein said rich solvent leaving from the bottom of said column is let down in pressure to a pressure level that is consistent with the operation of a distillation column for conducting said distilling of said step B.

10. The process of claim 9, wherein said rich solvent is heated before entering said distillation column in order to lower the reboiler heat load on said distillation column.

11. The process of claim 10, wherein said distillation column is a fractionation-type column which separates recovered hydrocarbons from said physical solvent.

12. The process of claim 11, wherein said recovered hydrocarbons leave the top of said distillation column and are condensed to form liquid hydrocarbon product and lean solvent leaves from the bottom of said distillation column.

13. The process of claim 12, wherein the temperature at the bottom of said distillation column is selected to ensure the recovery of all desirable hydrocarbons and is no higher than the boiling point of said physical solvent at said operating pressure.

14. The process of claim 13, wherein said column overhead is refluxed with a portion of said liquid hydrocarbon product in order to minimize loss of said physical solvent with said hydrocarbon gas liquid product.

15. The process of claim 14, wherein said lean physical solvent is cooled before recycling to said step A as said preferential physical solvent.

16. The process of claim 10, wherein said rich solvent is heated by lean/rich solvent heat exchanging.

* * * * *

UNITED STATES PATENT AND TRADEMARK OFFICE
CERTIFICATE OF CORRECTION

PATENT NO. : 4,617,038

DATED : October 14, 1986

INVENTOR(S) : Yuv R. Mehra

It is certified that error appears in the above-identified patent and that said Letters Patent is hereby corrected as shown below:

Abstract, line 6, "bottom" should read -- bottoms --.

Column 3, line 36, "columr" should read -- column --.

Column 4, line 63, "Chd 2+" should read -- $C_2^+$ --.

Signed and Sealed this

Third Day of March, 1987

Attest:

DONALD J. QUIGG

Attesting Officer

Commissioner of Patents and Trademarks